(12) United States Patent
Morishima et al.

(10) Patent No.: US 11,229,350 B2
(45) Date of Patent: Jan. 25, 2022

(54) ENDOSCOPE WITH BENDABLE INSERTION UNIT

(71) Applicant: HOYA CORPORATION, Tokyo (JP)

(72) Inventors: Takayoshi Morishima, Tokyo (JP); Kohei Iketani, Saitama (JP); Keiji Ito, Saitama (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 16/499,751

(22) PCT Filed: Jul. 3, 2017

(86) PCT No.: PCT/JP2017/024395
§ 371 (c)(1),
(2) Date: Sep. 30, 2019

(87) PCT Pub. No.: WO2018/220867
PCT Pub. Date: Dec. 6, 2018

(65) Prior Publication Data
US 2020/0046202 A1 Feb. 13, 2020

Related U.S. Application Data

(60) Provisional application No. 62/513,903, filed on Jun. 1, 2017.

(51) Int. Cl.
*A61B 1/005* (2006.01)
*A61B 1/00* (2006.01)
(Continued)

(52) U.S. Cl.
CPC ............ *A61B 1/0051* (2013.01); *A61B 1/005* (2013.01); *A61B 1/00009* (2013.01);
(Continued)

(58) Field of Classification Search
CPC ..... A61B 1/0051; A61B 1/0057; A61B 1/005; A61B 1/00071; A61B 1/00078;
(Continued)

(56) References Cited

U.S. PATENT DOCUMENTS 4,245,624 A * 1/1981 Komiya ............. A61B 1/00098
600/106
4,779,130 A * 10/1988 Yabe ........................ A61B 1/05
348/76

(Continued)

FOREIGN PATENT DOCUMENTS

EP 2151183 A1 2/2010
EP 2596738 A1 5/2013
(Continued)

OTHER PUBLICATIONS

English translation of International Search Report dated Aug. 1, 2017, in international application No. PCT/JP2017/024394.
(Continued)

*Primary Examiner* — John P Leubecker
(74) *Attorney, Agent, or Firm* — Kilpatrick Townsend & Stockton LLP

(57) ABSTRACT

The resin tube is a porous resin that has a porosity changing in a radial direction from a larger porosity at the center of the tube to a non-porous resin layer on a radially outer surface of the tube.

8 Claims, 22 Drawing Sheets

(51) Int. Cl.
*A61B 1/05* (2006.01)
*A61B 1/06* (2006.01)

(52) U.S. Cl.
CPC ...... *A61B 1/00071* (2013.01); *A61B 1/00091* (2013.01); *A61B 1/00096* (2013.01); *A61B 1/00098* (2013.01); *A61B 1/053* (2013.01); *A61B 1/00103* (2013.01); *A61B 1/051* (2013.01); *A61B 1/0684* (2013.01)

(58) Field of Classification Search
CPC . A61B 1/00101; A61B 1/00124; A61B 1/053; A61B 1/051; A61B 1/00103
USPC .......................................................... 600/144
See application file for complete search history.

(56) References Cited

U.S. PATENT DOCUMENTS

| | | | | |
|---|---|---|---|---|
| 5,168,864 | A * | 12/1992 | Shockey | A61B 1/0056 600/131 |
| 6,095,970 | A * | 8/2000 | Hidaka | A61B 1/00124 600/109 |
| 6,450,948 | B1 * | 9/2002 | Matsuura | A61B 1/0055 600/139 |
| 6,458,076 | B1 * | 10/2002 | Pruitt | A61B 1/0051 600/128 |
| 8,398,540 | B2 * | 3/2013 | Hassidov | A61B 1/00121 600/109 |
| 8,808,169 | B2 * | 8/2014 | Macnamara | A61B 1/0057 600/149 |
| 2003/0216615 | A1 * | 11/2003 | Ouchi | A61B 1/00078 600/121 |
| 2005/0272975 | A1 * | 12/2005 | McWeeney | A61M 25/0068 600/113 |
| 2006/0217594 | A1 * | 9/2006 | Ferguson | A61B 1/0676 600/175 |
| 2006/0253102 | A1 * | 11/2006 | Nance | A61M 25/0023 604/525 |
| 2007/0118019 | A1 | 5/2007 | Mitani et al. | |
| 2010/0010314 | A1 * | 1/2010 | Krattiger | A61B 1/0615 600/182 |
| 2011/0118628 | A1 * | 5/2011 | Zhou | A61M 25/09 600/585 |
| 2011/0224494 | A1 * | 9/2011 | Piskun | A61B 1/0125 600/205 |
| 2013/0131452 | A1 * | 5/2013 | Kuroda | A61B 1/00103 600/136 |
| 2013/0172670 | A1 | 7/2013 | Levy et al. | |
| 2013/0178705 | A1 * | 7/2013 | Takeuchi | A61B 1/0052 600/144 |
| 2014/0358140 | A1 * | 12/2014 | Emmons | A61N 7/022 606/33 |
| 2019/0254504 | A1 * | 8/2019 | Ide | A61B 1/0057 |
| 2020/0170489 | A1 * | 6/2020 | Takahashi | A61B 1/0055 |

FOREIGN PATENT DOCUMENTS

| | | | |
|---|---|---|---|
| JP | 2-246920 | A | 10/1990 |
| JP | 4-261635 | A | 9/1992 |
| JP | 6-254047 | A | 9/1994 |
| JP | 7-327923 | A | 12/1995 |
| JP | 8-24208 | A | 1/1996 |
| JP | 8-112245 | A | 5/1996 |
| JP | 2002-236260 | A | 8/2002 |
| JP | 2004-229947 | A | 8/2004 |
| JP | 2006-15076 | A | 1/2006 |
| JP | 2006-75238 | A | 3/2006 |
| JP | 2006-116128 | A | 5/2006 |
| JP | 2006-149689 | A | 6/2006 |
| JP | 2006-149844 | A | 6/2006 |
| JP | 2006-296675 | A | 11/2006 |
| JP | 2006325691 | A | 12/2006 |
| JP | 2006340878 | A | 12/2006 |
| JP | 2007-530155 | A | 11/2007 |
| JP | 2009-148420 | A | 7/2009 |
| JP | 4676427 | B2 | 4/2011 |
| JP | 2013-123647 | A | 6/2013 |
| WO | WO-9315648 | A1 * | 8/1993 ........... A61B 1/0052 |
| WO | 2004/086957 | A2 | 10/2004 |
| WO | 2005094665 | A2 | 10/2005 |
| WO | 2014111943 | A2 | 7/2014 |
| WO | 2016/199478 | A1 | 12/2016 |

OTHER PUBLICATIONS

English translation of International Search Report dated Aug. 22, 2017, in international application No. PCT/JP2017/024395.
English translation of International Search Report dated Aug. 21, 2018, in international application No. PCT/JP2018/021015.
EP17911415.2, Partial Supplemental European Search Report, dated Feb. 25, 2020, 9 pages.

\* cited by examiner

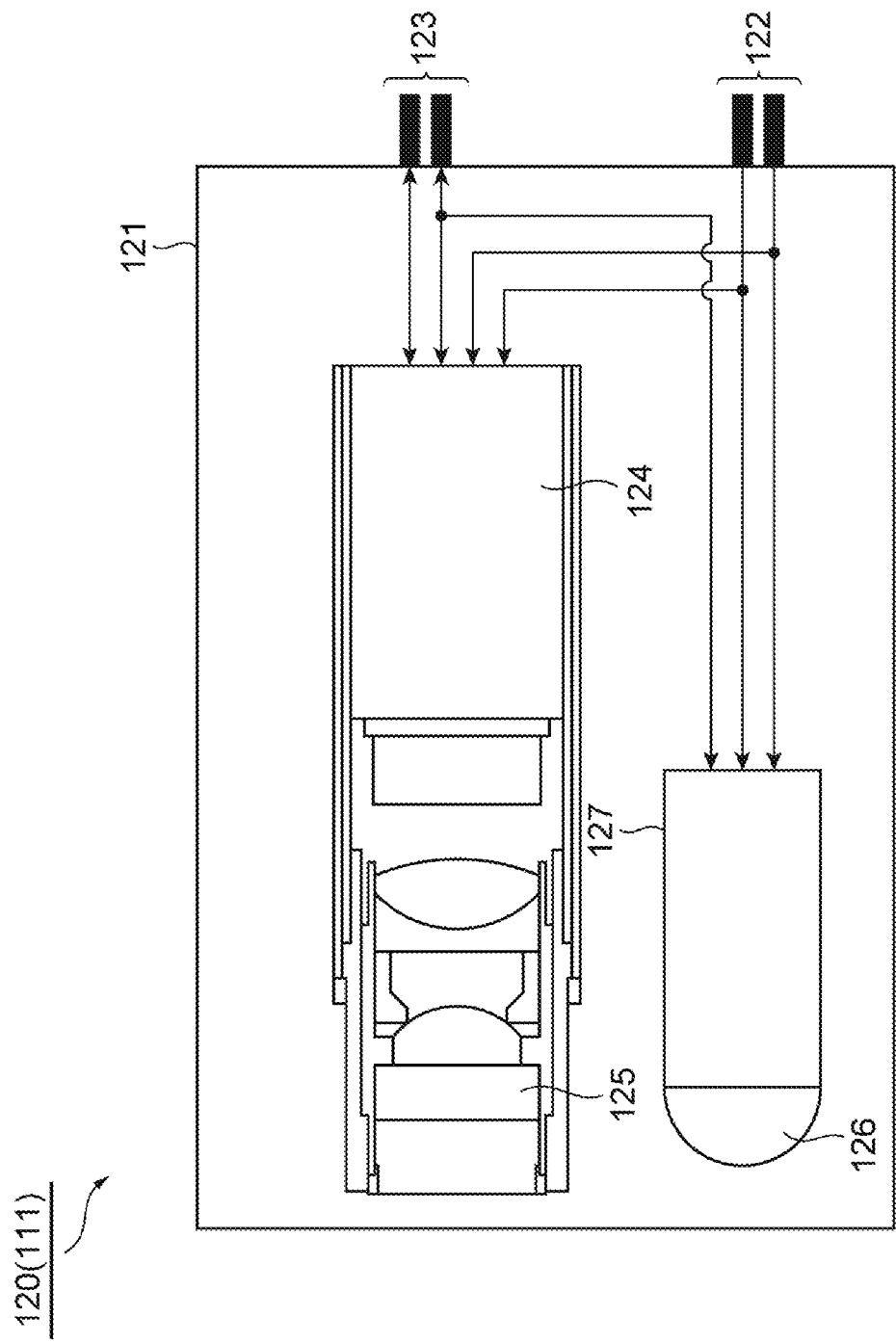

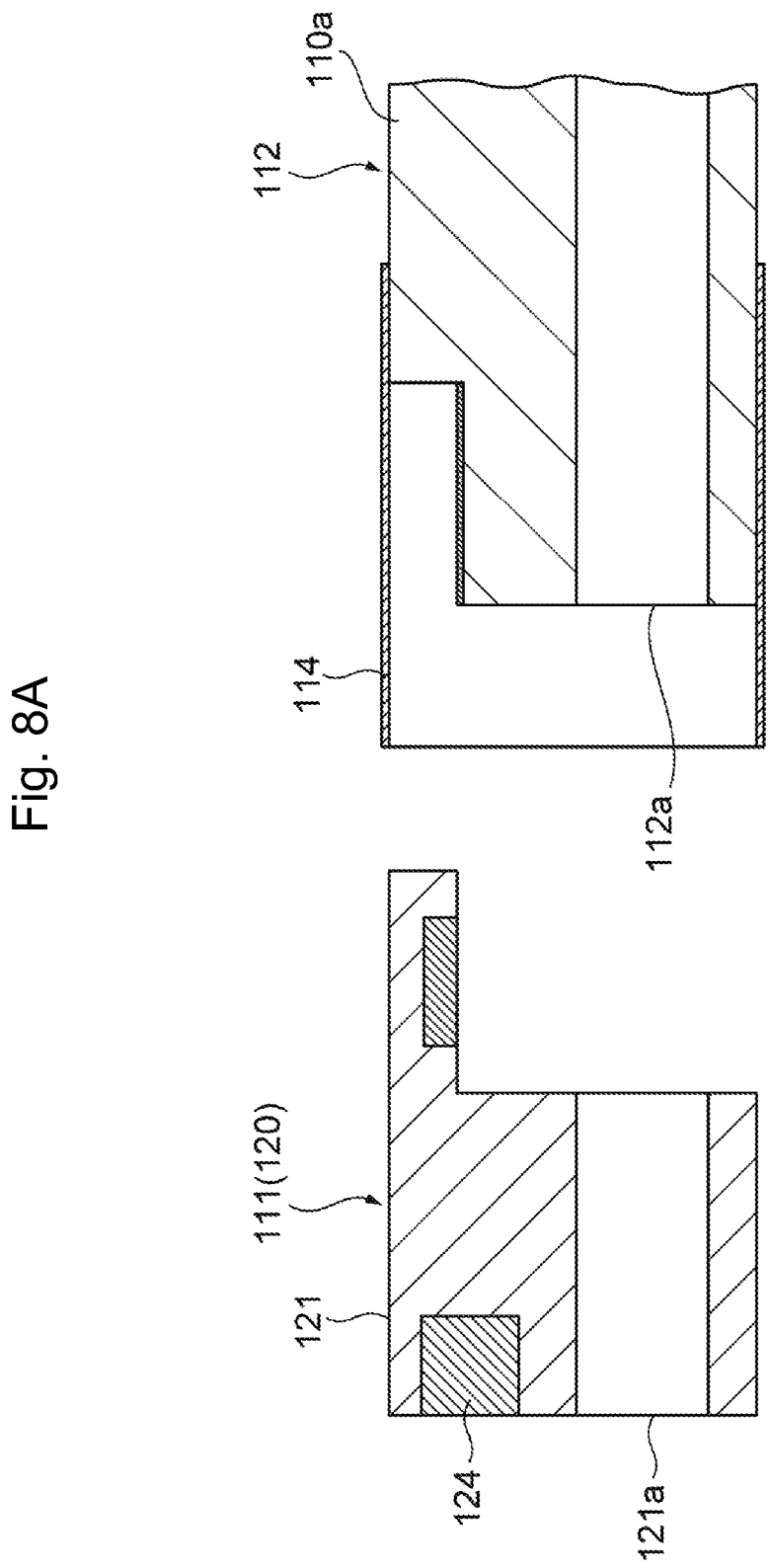

Fig. 11
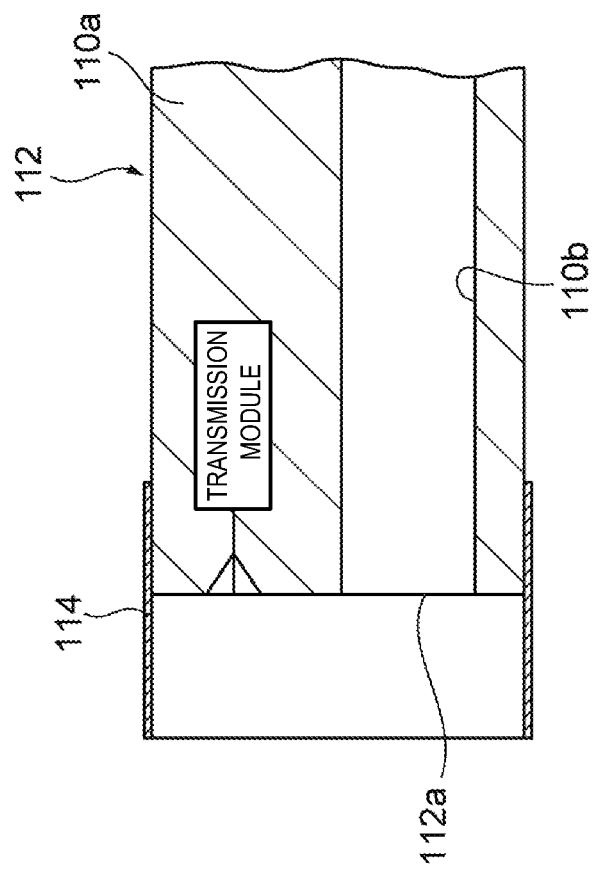
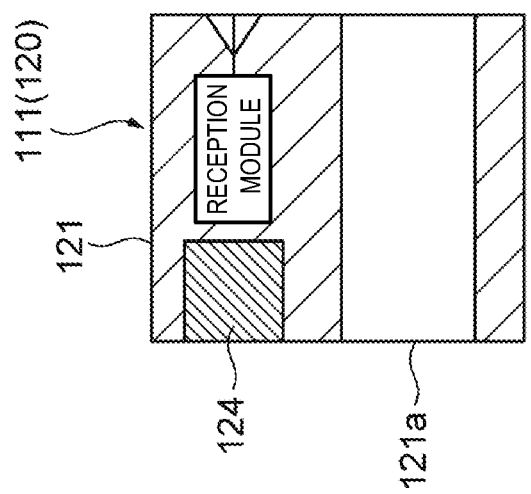

ENDOSCOPE WITH BENDABLE INSERTION UNIT

This application is the national phase application under 35 U.S.C. § 371 of international application No. PCT/JP2017/024395, filed Jul. 3, 2017, which claims priority based on U.S. provisional application 62/513,903, filed Jun. 1, 2017, in the United States, the contents of which are incorporated herein by reference.

TECHNICAL FIELD

The present disclosure relates to an endoscope.

BACKGROUND ART

In the related art, there is known an invention related to an endoscope flexible tube having excellent resistance to autoclave sterilization (see Patent Literature 1 below). The endoscope flexible tube disclosed in Patent Literature 1 is provided with a spiral tube, a mesh tube placed on the spiral tube, and an outer skin covering the outer periphery of the mesh tube. In this endoscope flexible tube, at least the outer surface of the outer skin contains a thermoplastic elastomer compounded with 0.5 to 50% by weight of a fullerene compound (see, for example, claim 1 in Patent Literature 1).

CITATION LIST

Patent Literature

Patent Literature 1: JP 2006-116128 A

SUMMARY OF INVENTION

Technical Problem

In recent years, there is growing demand for price reduction of endoscopes. However, depending on materials used for an insertion unit in an endoscope, the endoscope may reduce in operability and insertability and may increase in cost.

Accordingly, the present disclosure provides an endoscope that enables cost containment without deteriorating operability and insertability.

Solution to Problem

An endoscope according to the present disclosure is an endoscope provided with an insertion unit including an imaging unit and an operation unit configured to bend a part of the insertion unit, wherein at least a part of the insertion unit includes a tube formed of a resin, the tube including a plurality of channels formed of the resin included in the tube.

The endoscope may be provided with a single-use portion including the tube that is replaced for each use and a reusable portion including the imaging unit that is collected for each use to be reused.

The insertion unit may include a distal tip including the imaging unit, a bending section that is bent by the operation unit, and a flexible section disposed between the bending section and the operation unit, and at least a part of the bending section and a part of the flexible section may include the tube, and the resin excluding the channels may have a porosity of 0% or more and 80% or less.

The resin in the bending section may have an average porosity larger than an average porosity of the resin in the flexible section.

At least a part of the resin included in the tube may be a porous resin.

The porous resin may have a porosity changing in an axial direction or in a radial direction of the tube.

The endoscope may be provided with a rigid member inserted through the channels and an angle wire inserted through the rigid member and connected to a bending mechanism of the bending section, and the operation unit may be configured to operate the angle wire.

The rigid member may have flexural rigidity higher than flexural rigidity of the tube, being inserted through the channels in the flexible section.

The insertion unit may include a breaking section that is broken when the imaging unit is removed.

Advantageous Effects of Invention

According to the present disclosure, it is possible to provide an endoscope that enables cost containment without deteriorating operability and insertability.

BRIEF DESCRIPTION OF DRAWINGS

FIG. 6 is a schematic cross-sectional view illustrating an exemplary configuration of the imaging unit illustrated in FIG. 5.

FIG. 8A is an enlarged cross-sectional view illustrating a second modification of the endoscope illustrated in FIGS. 1 and 2.

FIG. 11 is an enlarged cross-sectional view illustrating a fifth modification of the endoscope illustrated in FIGS. 1 and 2.

DESCRIPTION OF EMBODIMENTS

Figure 1:
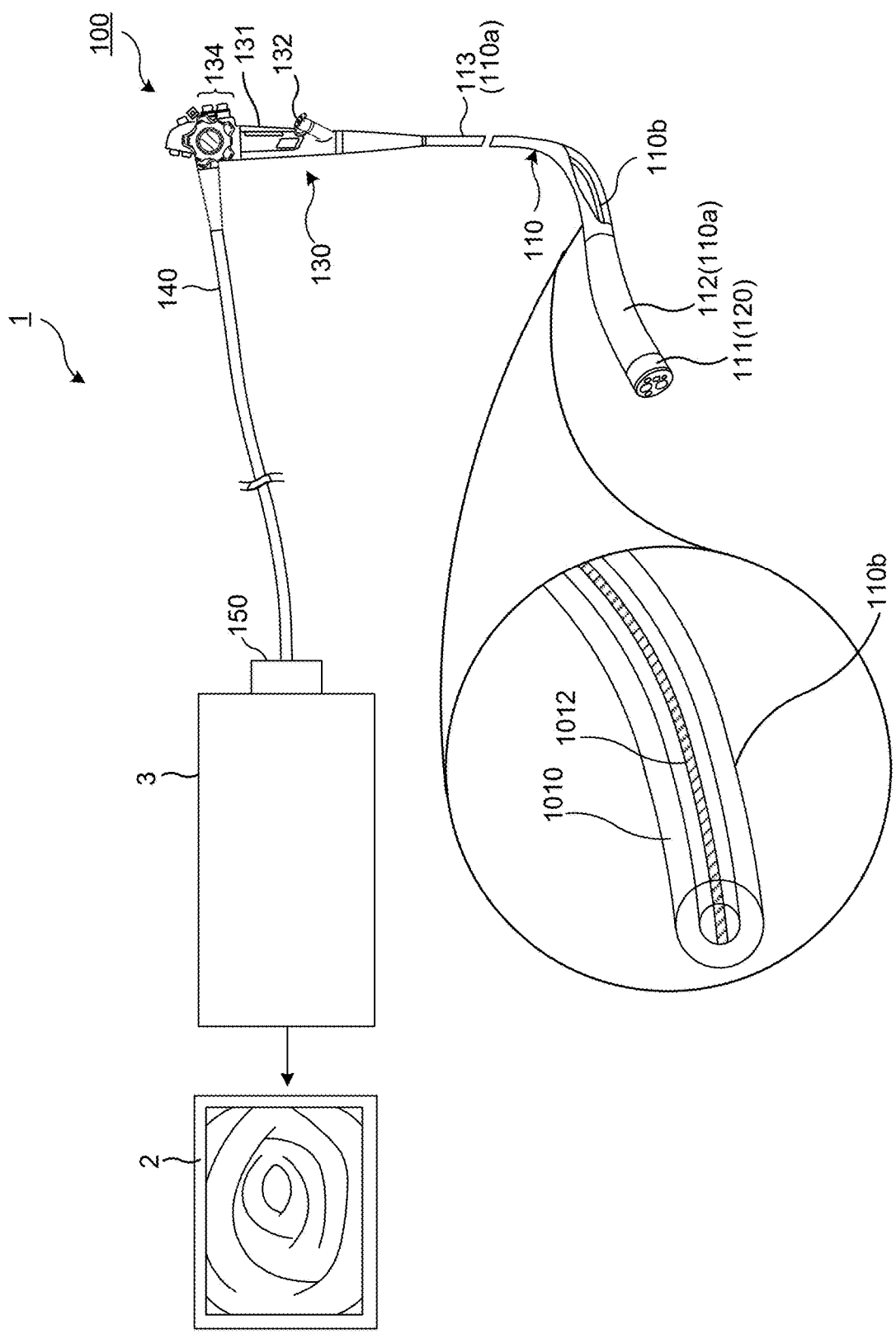
FIG. 1 is a schematic configuration diagram illustrating an endoscope system according to an embodiment of the present disclosure.

Hereinafter, embodiments of the present disclosure will be described with reference to the drawings. In the accompanying drawings, functionally identical elements may be denoted by the same reference numerals. In the following description, "axial direction" indicates an axial direction of an insertion unit in an endoscope, "front side" indicates the side close to a subject, and "rear side" indicates the side close to an operation unit of the endoscope.

<Configuration of Endoscope System>

FIG. 1 is a schematic configuration diagram illustrating an endoscope system 1 according to this embodiment. In FIG. 1, for sake of simplicity, a connection between devices is indicated by an arrow.

The endoscope system 1 of this embodiment is provided with, for example, a monitor 2, a processor 3, and an endoscope 100.

The endoscope 100 is provided with an insertion unit 110 that is inserted through a subject and an operation unit 130 that bends a part of the insertion unit 110. Although details will be described later, in the endoscope 100 of this embodiment, at least a part of the insertion unit 110 includes a tube 110a formed of a resin.

Furthermore, the tube 110a includes a plurality of channels 110b formed of the resin included in the tube 110a.

More specifically, the insertion unit 110 is provided with, for example, a distal tip 111 that includes an imaging unit 120, a bending section 112 that is bent by the operation unit 130, and a flexible section 113 that is disposed between the bending section 112 and the operation unit 130. At least a part of the bending section 112 and a part of the flexible section 113 include the tube 110a. The resin included in the tube 110a excluding the channels 110b has a porosity of, for example, 0% or more and 80% or less.

The plurality of channels 110b of the tube 110a of the insertion unit 110 of the endoscope 100 includes, for example, a cable channel through which a signal cable for imaging is inserted. The plurality of channels 110b of the tube 110a also includes, for example, a treatment tool channel for inserting a treatment tool such as forceps, an air supply channel for supplying air, a water supply channel and a secondary water supply channel for supplying water. The plurality of channels 110b of the tube 110a may also include, for example, a lighting channel through which a light guide fiber bundle for lighting is inserted.

The endoscope 100 is provided with, for example, a rigid member 1010 inserted through the channels 110b of the tube 110a of the insertion unit 110 and provided with an angle wire 1012 inserted through the rigid member 1010 and connected to a bending mechanism of the bending section 112. Examples of the rigid member 1010 include a guide tube and a metallic close coil. The operation unit 130 is configured to operate the angle wire 1012. As the bending mechanism, for example, a known bending mechanism that bends an insertion unit of a known endoscope is applicable.

The endoscope 100 is provided with a connector cable 140 extending from the operation unit 130 and a connector unit 150 disposed at an end of the connector cable 140.

The connector unit 150 is connected to the processor 3. The processor 3 is a device for processing image data input from the endoscope 100 and producing a video signal. The monitor 2 is connected to the processor 3. The monitor 2 displays an internal image of the subject imaged by the endoscope 100 and produced by the processor 3.

<Endoscope>

Figure 2:
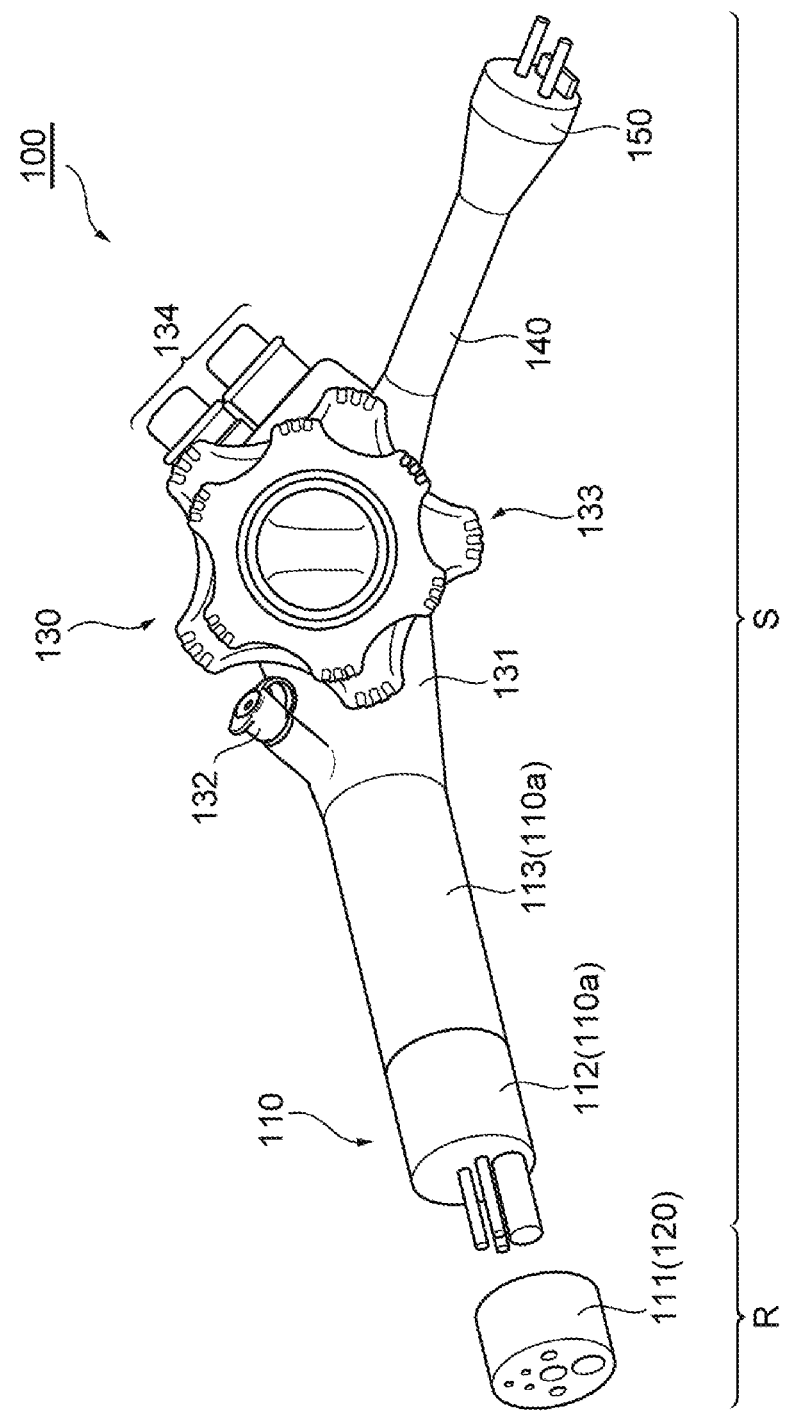
FIG. 2 is a schematic perspective view illustrating the overall configuration of the endoscope illustrated in FIG. 1.

FIG. 2 is a schematic perspective view illustrating the overall configuration of the endoscope 100 illustrated in FIG. 1. Hereinafter, the configuration of the endoscope 100 will be described in more detail with reference to FIG. 2. The position and shape of the operation unit 130 in the endoscope 100 may be different from the actual position and shape for the purpose of illustration.

As described above, the endoscope 100 is provided with the insertion unit 110 and the operation unit 130 that bends a part of the insertion unit 110. The insertion unit 110 is provided with, for example, the distal tip 111 that includes the imaging unit 120, the bending section 112 that is bent by the operation unit 130, and the flexible section 113 that is disposed between the bending section 112 and the operation unit 130.

In the endoscope 100 of this embodiment, as described above, at least a part of the insertion unit 110 includes the resinous tube 110a having the plurality of channels 110b, that is, for example, a multi-lumen tube having pliability and flexibility. More specifically, at least a part of the bending section 112 and a part of the flexible section 113 includes the resinous tube 110a having the plurality of channels 110b. The resin included in the tube 110a has a porosity of, for example, 0% to 80%.

The resin in the bending section 112 may have an average porosity, for example, larger than that of the resin in the flexible section 113. Here, an average porosity of a certain part of resin indicates an average porosity of the whole resin included in the part.

In the example illustrated in FIGS. 1 and 2, the distal tip 111 of the insertion unit 110 includes the imaging unit 120. However, the distal tip 111 of the insertion unit 110 may include the tube 110a, and the imaging unit 120 may be disposed inside the tube 110a of the distal tip 111.

The endoscope 100 of this embodiment is, for example, a single-use endoscope provided with a single-use portion S and a reusable portion R. The single-use portion S includes, for example, the tube 110a included in at least a part of the insertion unit 110. Every time the endoscope 100 is used, the single-use portion S is replaced. The reusable portion R includes, for example, the imaging unit 120. Every time the endoscope 100 is used, the reusable portion R is collected, cleaned, sterilized, and disinfected for reuse.

The single-use portion S may be the tube 110a of the insertion unit 110, or may be the entire insertion unit 110 including the tube 110a. Alternatively, the single-use portion S may be a part of the insertion unit 110 including the tube 110a. The single-use portion S may also include the operation unit 130, the connector cable 140, and the connector unit 150. Furthermore, the bending section 112 may include one tube 110a, being formed in an integrated manner with the flexible section 113. Alternatively, the bending section 112 may include another tube 110a different from the tube 110a included in the flexible section 113. Each part of the single-use portion S is preferably formed of a resin to the extent possible from a viewpoint of cost reduction.

The reusable portion R may include the imaging unit 120 exclusively or may include a part of the insertion unit 110 excluding the tube 110a. For example, the reusable portion R may include the bending section 112. The reusable portion R may include a part or all of the operation unit 130, the connector cable 140, and the connector unit 150.

The resin included in the tube 110a may be a non-porous resin as a whole, or a solid resin which is not a porous resin. However, at least a part of the resin included in the tube 110a may be a porous resin. It is possible to produce the tube 110a, for example, by extrusion molding of a resin material.

Examples of the porous resin included in the tube 110a include polytetrafluoroethylene (PTFE), expanded PTFE (ePTFE), polyethylene (PE), high density polyethylene (HDPE), and polypropylene (PP). Examples of the non-porous resin included in the tube 110a include polyurethane (PU), polypropylene (PP), polyethylene (PE), and polyamide.

The porous resin included in the tube 110a excluding the channels 110b has a porosity of, for example, from 0% to 80%. The porosity of the porous resin varies, for example, about ±5%. From a viewpoint of facilitating the production of the tube 110a, the porosity of the porous resin is preferably 15% or more. When using the porous resin tube 110a for the bending section 112, the porosity of the porous resin is set to, for example, 20% or more and 80% or less.

More specifically, the porosity of the porous resin in the bending section 112 is set, for example, in the following manner according to a material and an outer diameter of the porous resin. Here, provided that the material of the porous resin is PTFE. In this case, the outer diameter of the tube 110a included in the bending section 112 and the porosity of the porous resin are set as shown in Table 1 below. Accordingly, the bending section 112 improves in pliability and flexibility, which enables the bending section 112 to have flexural rigidity appropriate for bending operation.

TABLE 1

| Outer diameter of tube | Porosity of porous resin |
| --- | --- |
| φ8 mm to φ9 mm | 30% to 50% |
| φ9 mm to φ10 mm | 40% to 60% |
| φ10 mm to φ11 mm | 50% to 70% |
| φ11 mm to φ13 mm | 60% or more and 80% or less |

The tube 110a of the insertion unit 110, for example, may be compressed constantly in the axial direction between the imaging unit 120 and the operation unit 130. Such a state improves the tube 110a in density and improves the insertion unit 110 in flexural rigidity.

In the tube 110a of the insertion unit 110, the porous resin may have a porosity changing in the axial direction or in a radial direction of the tube 110a. For example, in the tube 110a of the insertion unit 110, the porous resin may have a porosity changing in the radial direction of the tube 110a. More specifically, in the radial direction of the tube 110a, the outer surface of the tube 110a may have a porosity smaller than that of the center of the tube 110a.

In the radial direction of the tube 110a, the porosity may decrease continuously or gradually from the center toward the outer surface. In the radial direction of the tube 110a, the porosity may decrease continuously or gradually from the outer surface toward the center. The gradual change in porosity includes a discontinuous change in porosity. Here, the discontinuous change in porosity indicates that there is a part with a porosity unchanging between parts with a porosity changing, or indicates that the porosity changes stepwise.

Furthermore, the tube 110a may include a non-porous resin layer having a porosity of 0% on the radially outer surface and in a part close to the outer surface. Such a configuration prevents liquid infiltration from the outer surface of the insertion unit 110. Still further, the tube 110a may include a non-porous resin layer having a porosity of 0% on the inner wall of the channels 110b and in a part close to the inner wall. Such a configuration prevents liquid infiltration from the inner wall of the channels 110b of the insertion unit 110.

In the axial direction of the tube 110a, that is, from an end close to the operation unit 130 or a proximal end of the insertion unit 110 to the distal tip 111 of the insertion unit 110, the porous resin included in the tube 110a may have a porosity changing continuously or gradually. For example, as described above, in the axial direction of the tube 110a, the resin in the bending section 112 may have an average porosity, for example, larger than that of the resin in the flexible section 113.

The gradual change in porosity in the axial direction includes a discontinuous change in porosity in the radial direction. Here, the discontinuous change in porosity indicates that there is a part with a porosity unchanging between parts with a porosity changing, or indicates that the porosity changes stepwise. A material of the tube 110a in a part connected to the operation unit 130 of the insertion unit 110 may be, for example, a non-porous resin having a porosity of 0%.

FIGS. 3A to 3F are graphs illustrating examples of flexural rigidity of the tube 110a of the insertion unit 110. In the graphs illustrated in FIGS. 3A to 3F, the flexural rigidity of the tube 110a is taken along the ordinate, and the distance from the distal tip of the insertion unit 110 is taken along the abscissa.

Figure 3A:
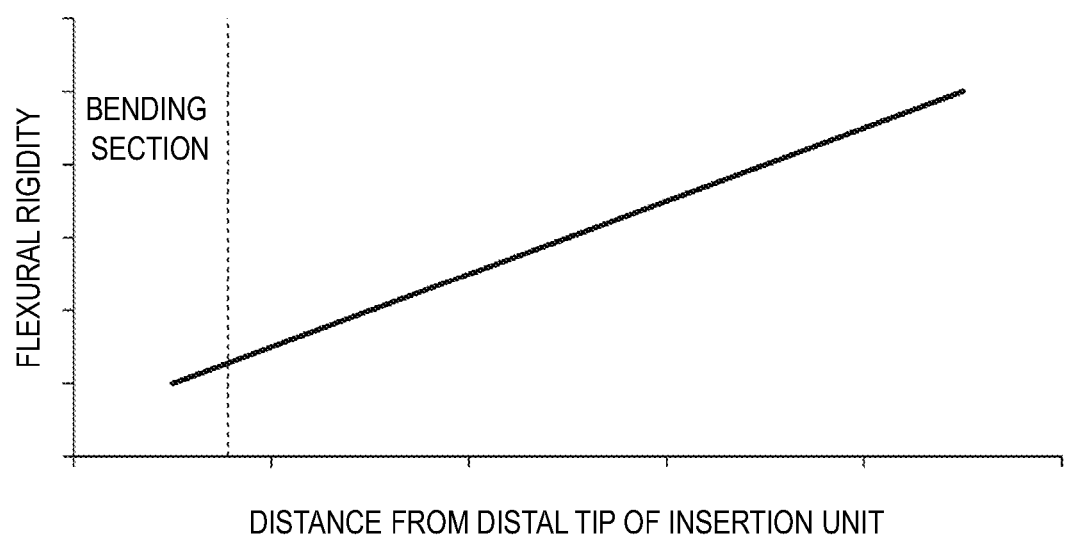
FIG. 3A is a graph illustrating flexural rigidity of a tube of an insertion unit illustrated in FIG. 2.

In the example illustrated in FIG. 3A, the porous resin in the tube 110a has a porosity continuously decreasing at a substantially constant rate from a distal tip in which the bending section 112 is disposed to a proximal end which is connected to the operation unit 130. Accordingly, the tube 110a alone included in the insertion unit 110 has flexural rigidity increasing at a substantially constant rate from the distal tip to the proximal end.

As described above, when the guide tube for inserting the angle wire is inserted through the channels 110b of the tube 110a of the insertion unit 110, the guide tube may have flexural rigidity higher than that of the tube 110a. In this case, the guide tube may be inserted through the channels 110b of the tube 110a on the side closer to the proximal end than the bending section 112 of the insertion unit 110, that is, on the side closer to the operation unit 130 than the bending section 112.

Figure 3B:
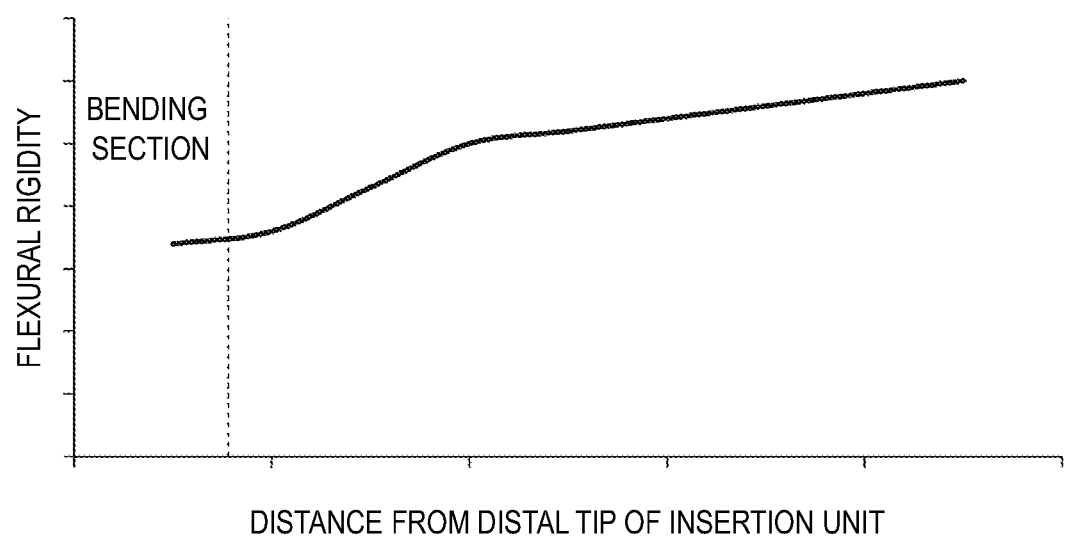
FIG. 3B is a graph illustrating flexural rigidity of the tube of the insertion unit illustrated in FIG. 2.
Figure 3C:
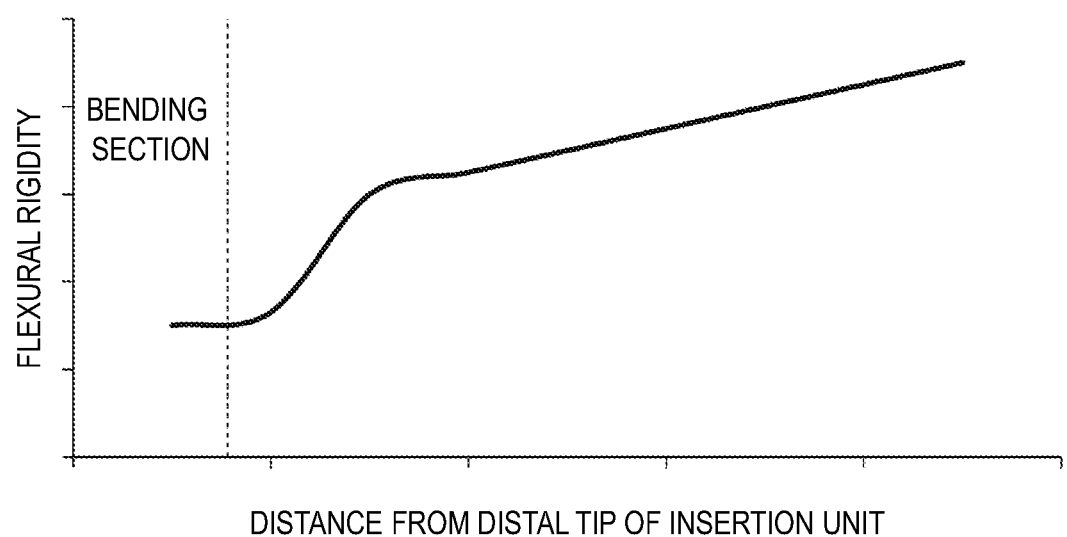
FIG. 3C is a graph illustrating flexural rigidity of the tube of the insertion unit illustrated in FIG. 2.

In the tube 110a of the example illustrated in FIG. 3B, as in the example illustrated in FIG. 3A, the porous resin has a porosity continuously decreasing at a substantially constant rate from the distal tip to the proximal end. In this example, four guide tubes are inserted through the channels 110b at the flexible section 113 closer to the proximal end than the bending section 112 of the insertion unit 110. The guide tube has flexural rigidity higher than that of the tube 110a. Therefore, compared to the example illustrated in FIG. 3A, in the example illustrated in FIG. 3B, the tube 110a has high flexural rigidity in a part closer to the proximal end than the bending section 112 of the insertion unit 110. In addition to the guide tube, a rigid member having flexural rigidity higher than that of the tube 110a may be inserted through the channels 110b of the tube 110a so as to improve the flexural rigidity of the tube 110a, In the tube 110a in the example illustrated in FIG. 3C, the porous resin has a porosity at a relatively high constant value on the side close to the distal tip 111 where the bending section 112 is disposed, and in the flexible section 113 closer to the proximal end than the bending section 112, the porous resin has a porosity continuously decreasing from the distal tip to the proximal end. Accordingly, the flexural rigidity of the tube 110a alone is set to a relatively low constant value in the bending section 112, increasing continuously from the distal tip to the proximal end in the flexible section 113 closer to the proximal end than the bending section 112.

Figure 3D:
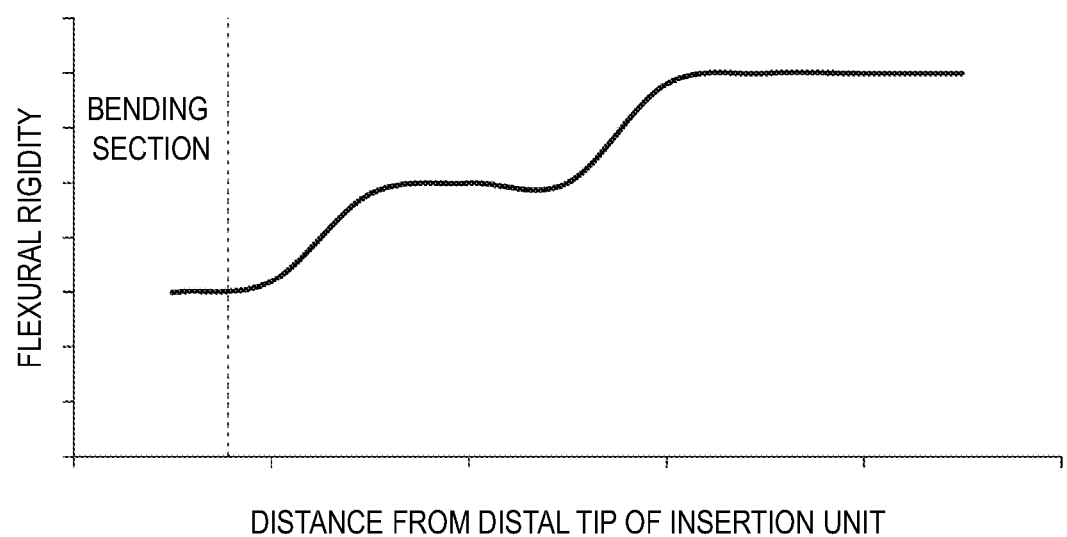
FIG. 3D is a graph illustrating flexural rigidity of the tube of the insertion unit illustrated in FIG. 2.

In the example illustrated in FIG. 3D, in the tube 110a, the porous resin has a porosity gradually decreasing in two stages from the distal tip to the proximal end. Accordingly, the tube 110a alone included in the insertion unit 110 has flexural rigidity increasing in two stages from the distal tip to the proximal end.

Figure 3E:
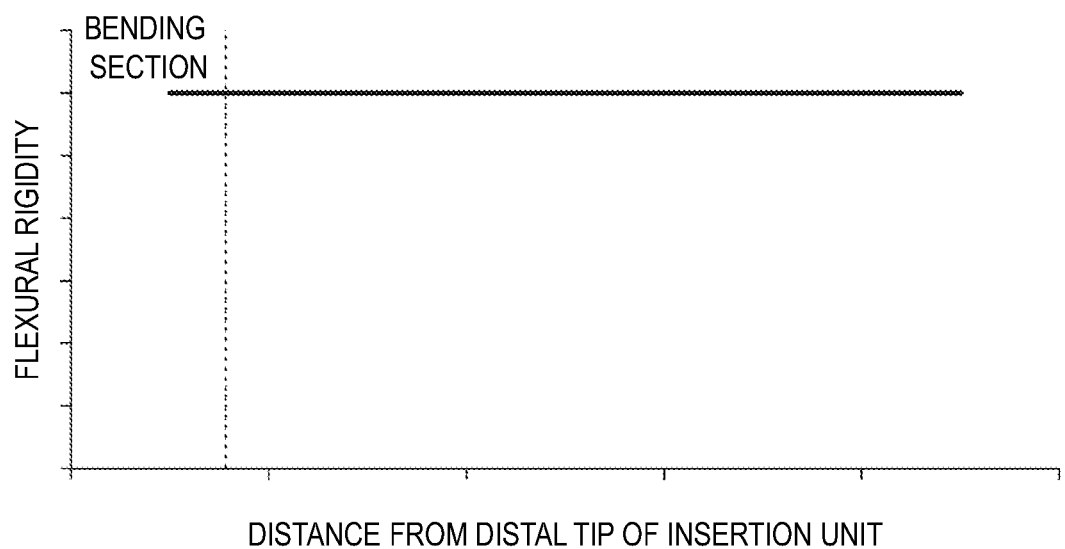
FIG. 3E is a graph illustrating flexural rigidity of the tube of the insertion unit illustrated in FIG. 2.

In the example illustrated in FIG. 3E, the tube 110a includes a non-porous resin, or a solid resin, from the distal tip to the proximal end, having a porosity of 0%. Therefore, the flexural rigidity of the tube 110a alone included in the insertion unit 110 is constant from the distal tip to the proximal end and is higher than a case where the material of the tube 110a is a porous resin.

Figure 3F:
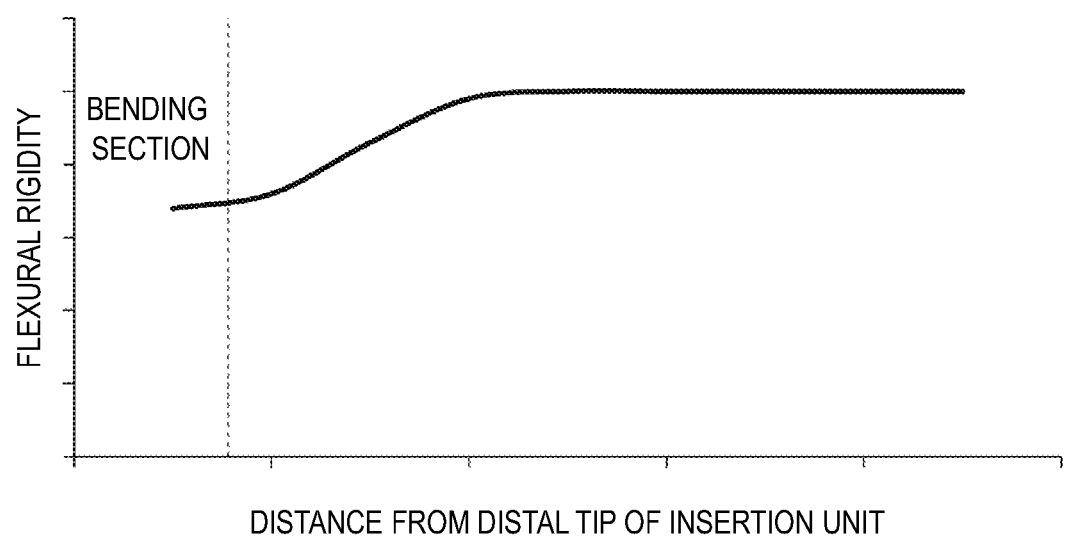
FIG. 3F is a graph illustrating flexural rigidity of the insertion unit illustrated in FIG. 2.

In the example illustrated in FIG. 3F, the tube 110a includes a non-porous resin from the distal tip to the proximal end as in the example illustrated in FIG. 3E, and the guide tube of the angle wire is inserted through the channels 110b as in the example illustrated in FIG. 3B. In the example illustrated in FIG. 3F, in addition to the guide tube, other members included in the insertion unit 110 are inserted through and disposed in the channels 110b, being included in the insertion unit 110. Therefore, compared to the example illustrated in FIG. 3E, in the example illustrated in FIG. 3F, the tube 110a has high flexural rigidity in a part closer to the proximal end than the bending section 112 of the insertion unit 110.

Figure 4:
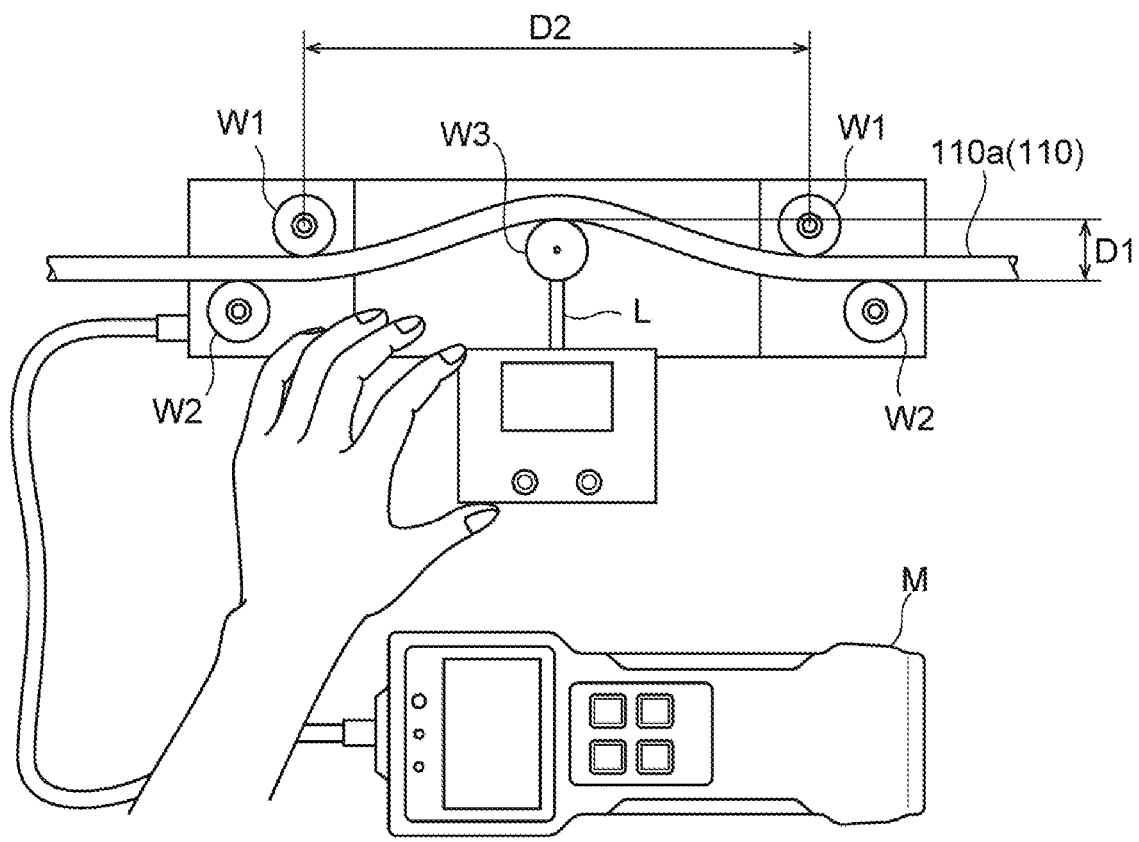
FIG. 4 is a view illustrating an example of a measurement method of flexural rigidity.

FIG. 4 is a view illustrating an example of a measurement method of flexural rigidity. It is possible to measure the flexural rigidity of the tube 110a alone included in the insertion unit 110, the flexural rigidity of the rigid member inserted through the tube 110a and the channels 110b, or the flexural rigidity of the insertion unit 110 including the tube 110a and other members, for example, in the following manner. First, the tube 110a is straightened and disposed between two pairs of rollers W1 and W2. Accordingly, the tube 110a is supported from both sides in the radial direction by the two pairs of rollers W1 and W2 which are separated in the axial direction.

Next, between the two pairs of rollers W1 and W2 in the axial direction of the tube 110a, a roller W3 is disposed on one side of the tube 110a in the radial direction. The roller W3 is pushed in the radial direction of the tube 110a at a predetermined amount of indentation D1 by a measuring rod L of a measuring instrument M so as to bend the tube 110a supported between the two pairs of rollers W1 and W2. In this state, a reaction force acting on the measuring rod L is measured by the measuring instrument M, and this reaction force is defined as the flexural rigidity of the tube 110a alone or that of the insertion unit 110. For example, when the tube 110a has an outer diameter of 0 mm, an interval D2 of the rollers W1 separated in the axial direction of the tube 110a is set to 200 mm, and the amount of indentation D1 is set to 20 mm.

As illustrated in FIG. 2, the operation unit 130 of the endoscope 100 includes an operation unit body 131 including a grip section, and a treatment tool inlet 132 disposed in the operation unit body 131 on the side close to the insertion unit 110. The treatment tool inlet 132 is an opening of the treatment tool channel disposed in the operation unit 130. The operation unit body 131 is provided with a bending operation knob 133 for bending the bending section 112, and switches 134 or the like associated with each operation of the endoscope 100. For example, the proximal end of the tube 110a of the insertion unit 110 is connected to the operation unit body 131.

Figure 5:
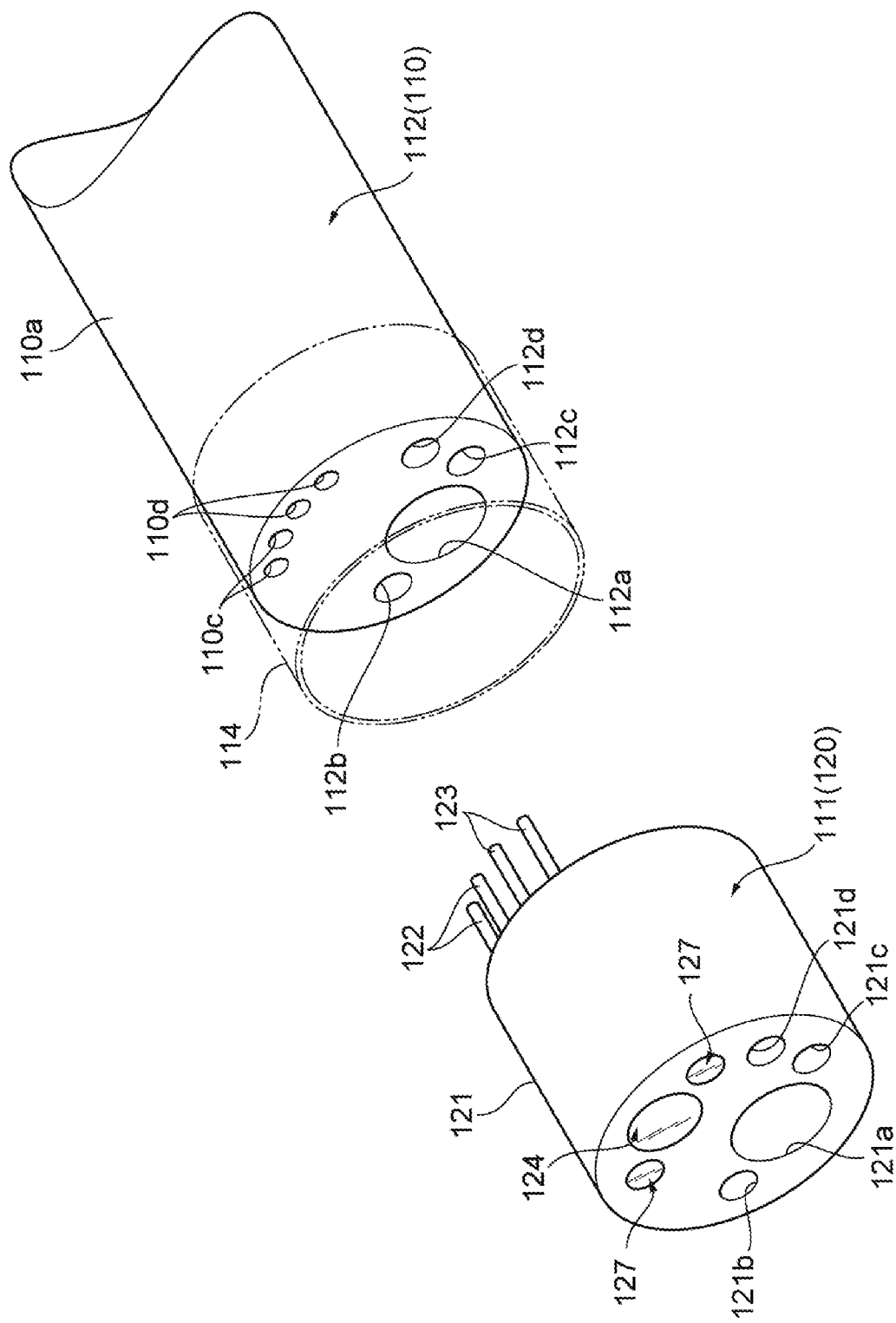
FIG. 5 is an enlarged view illustrating an example of an imaging unit of the endoscope illustrated in FIGS. 1 and 2.

FIG. 5 is an enlarged view illustrating an example of the imaging unit 120 of the endoscope 100 illustrated in FIG. 1 and FIG. 2. In the example illustrated in FIG. 5, at a distal tip of the bending section 112 that includes the tube 110a, the insertion unit 110 includes an opening 112a for the treatment tool channel, an opening 112b for the air supply channel, an opening 112c for the water supply channel, and an opening 112d for the secondary water channel.

At the distal tip of the tube 110a, the insertion unit 110 also includes a contact-type power connector 110c and a signal connector 110d. The power connector 110c is connected, for example, to a power terminal of the connector unit 150 through a power cable passing through the cable channel of the tube 110a. The signal connector 110d is connected, for example, to a signal terminal of the connector unit 150 through the signal cable passing through the cable channel of the tube 110a of the insertion unit 110.

The imaging unit 120 is provided with, for example, a cylindrical body section 121, and a forceps port 121a, an air supply port 121b, a water supply port 121c, and a secondary water supply port 121d disposed in the body section 121. The forceps port 121a, the air supply port 121b, the water supply port 121c, and the secondary water supply port 121d are openings for the treatment tool channel, the air supply channel, the water supply channel, and the secondary water supply channel disposed in the body section 121, respectively. The forceps port 121a, the air supply port 121b, the water supply port 121c, and the secondary water supply port 121d are respectively communicated with the treatment tool channel, the air supply channel, the water supply channel, and the secondary water supply channel disposed in the tube 110a through the openings 112a, 112b, 112c, and 112d of the tube 110a. The imaging unit 120 also includes a power pin 122 and a signal pin 123 at the rear end of the body section 121 connected to the distal tip of the tube 110a.

A joint between the imaging unit 120 and the insertion unit 110 is covered with a tube-shaped breaking section 114. Examples of a material of the breaking section 114 include a resin having pliability and flexibility as similar to the tube 110a of the insertion unit 110. The breaking section 114 covers not only the joint between the imaging unit 120 and the insertion unit 110 but also, for example, the rear end of the imaging unit 120 adjacent to the joint and the distal tip of the bending section 112. For example, the breaking section 114 is bonded or joined to the rear end of the imaging unit 120 and the distal tip of the bending section 112, and the breaking section 114 is broken when the imaging unit 120 included in the distal tip 111 of the insertion unit 110 is removed from the insertion unit 110.

FIG. 6 is a schematic cross-sectional view illustrating an exemplary configuration of the imaging unit 120 illustrated in FIG. 5. The imaging unit 120 includes at least an imaging element 124 such as CMOS or CCD. In this embodiment, the imaging unit 120 is provided with, for example, the imaging element 124, an objective lens 125, and a small LED lighting 127 including a lens 126. For example, the body section 121 closes and seals each part of the imaging unit 120 including the imaging element 124. The imaging unit 120 is provided with the power pin 122 and the signal pin 123 at the rear end of the body section 121. The imaging unit 120 does not have to include all the components illustrated in FIG. 6 and may include, for example, minimal components that enable reuse of the imaging element 124.

The power pin 122 is connected to, for example, the imaging element 124 and the small LED lighting 127. Inserting and connecting the power pin 122 to the power connector 110c disposed at the distal tip of the tube 110a enables electric power supply to the imaging element 124 and to the small LED lighting 127. Furthermore, the signal pin 123 is connected to, for example, the imaging element 124 and the small LED lighting 127. Inserting and connecting the signal pin 123 to the signal connector 110d disposed at the distal tip of the tube 110a enables output of an image signal of the imaging element 124 to the signal terminal of the connector unit 150 through the signal cable. The connection for outputting the image signal of the imaging element 124 is not limited to the contact method using pins and connectors and may be changed to, for example, wireless connection such as Bluetooth (registered trademark).

The body section 121 includes, for example, a hard resin different from the resin included in the tube 110a and having pliability. For example, a part or all of the body section 121 may be transparent. In this case, lenses such as the objective lens 125 and the lens 126 for lighting may be formed in an integrated manner with the body section 121. In a case where the imaging unit 120 includes the imaging element 124 alone, the imaging unit 120 does not necessarily include the body section 121. In this case, the imaging unit 120 includes the imaging element 124 sealed with a resin or the like, being embedded in the distal tip of the tube 110a included in the distal tip 111 of the insertion unit 110.

Hereinafter described is the operation of the endoscope 100 according to this embodiment.

As described above, the endoscope 100 according to this embodiment is provided with the insertion unit 110 including the imaging unit 120 and the operation unit 130 that bends a part of the insertion unit 110. At least a part of the insertion unit 110 includes the resinous tube 110a. Furthermore, the tube 110a includes a plurality of channels 110b formed of the resin included in the tube 110a.

In this manner, at least a part of the insertion unit 110 of the endoscope 100 is made to include the resinous tube 110a. Accordingly, characteristics of the tube 110a such as flexibility, pliability, and smoothness of the outer surface lead to prevention of deterioration in operability and insertability when the insertion unit 110 is inserted through the body of a patient. In addition, the tube 110a is made to include the plurality of channels 110b formed of the resin included in the tube 110a itself, that is to say, the resinous tube 110a is made to include the plurality of channels 110b, or for example, the tube 110a is made to be a multi-lumen tube. Such a configuration enables production of the insertion unit 110 with ease and with a relatively inexpensive material, which leads to cost reduction of the endoscope 100.

Furthermore, the endoscope 100 of this embodiment is provided with the insertion unit 110 and the operation unit 130 that bends a part of the insertion unit 110 as described above. The insertion unit 110 is provided with the distal tip 111 that includes the imaging unit 120, the bending section 112 that is bent by the operation unit 130, and the flexible section 113 that is disposed between the bending section 112 and the operation unit 130. Still further, at least a part of the bending section 112 and a part of the flexible section 113 include the resinous tube 110a provided with the plurality of channels. The tube 110a excluding the resin channels 110b has a porosity of 0% or more and 80% or less.

In this manner, at least a part of the bending section 112 and a part of the flexible section 113 is made to include the resinous tube 110a. Accordingly, characteristics of the tube 110a such as flexibility, pliability, and smoothness of the outer surface leads to prevention of deterioration in operability and insertability when the bending section 112 and the flexible section 113 are inserted through the body of a patient. In addition, the tube 110a excluding the resin channels 110b has a porosity of 0% or more and 80% or less. Accordingly, the bending section 112 and the flexible section 113 are imparted with flexural rigidity according to the porosity of the tube 110a.

For example, when the resin in the bending section 112 has an average porosity larger than that of the resin in the flexible section 113, the flexural rigidity of the tube 110a in the bending section 112 is made smaller than the flexural rigidity of the tube 110a in the flexible section 113. Such a configuration facilitates the operation to bend the bending section 112 and further improves operability of the endoscope 100.

The endoscope 100 of this embodiment is also provided with the single-use portion S including the tube 110a which is replaced for each use and the reusable portion R including the imaging unit 120 which is collected for each use to be reused. Accordingly, the single-use portion S including the relatively inexpensive tube 110a is discarded, which enables an endoscopic examination with a high level of cleanliness maintained.

Replacement of the single-use portion S including the tube 110a with a new one for each use saves labor such as cleaning, sterilization, and disinfection of the insertion unit 110, which reduces the risk of damaging or malfunctioning of the insertion unit 110. In addition, collecting of the reusable portion R including the relatively expensive imaging unit 120 for each use and cleaning, sterilization, and disinfection of the reusable portion R for reuse reduce maintenance costs of the single-use type endoscope 100 in which members other than the reusable portion R are discarded.

In the endoscope 100 of this embodiment, the insertion unit 110 includes the breaking section 114 that is broken when the imaging unit 120 is removed. Accordingly, for example, after the endoscope 100 is used, when a third party having no authority to replace the single-use portion S removes the imaging unit 120, the breaking section 114 is broken, and the endoscope 100 cannot be reformed. Therefore, it is possible to prevent reuse of the single-use portion S including the tube 110a and to prevent erroneous removal of the imaging unit 120. Thus, it is possible to improve traceability of the endoscope 100 and to further improve safety and reliability of the endoscope 100.

As described above, when the imaging unit 120 is embedded in the distal tip of the tube 110a included in the distal tip 111 of the insertion unit 110, the tube 110a serves as the breaking section 114. In other words, in order to collect the reusable portion R including the imaging unit 120, it is required to break the tube 110a and take out the imaging unit 120 disposed inside the tube 110a.

Accordingly, after the endoscope 100 is used, when a third party having no authority to replace the single-use portion S removes the imaging unit 120, the tube 110a is broken, and the endoscope 100 cannot be reformed. Therefore, it is possible to prevent reuse of the single-use portion S including the tube 110a and to prevent erroneous removal of the imaging unit 120. Thus, it is possible to improve traceability of the endoscope 100 and to further improve safety and reliability of the endoscope 100.

According to the endoscope 100 of this embodiment, the breaking section 114 or the tube 110a prevents the imaging unit 120 from being removed by an unauthorized third party. Even when the imaging unit 120 is removed, it is possible to determine easily that the imaging unit 120 is removed by the broken breaking section 114 or the broken tube 110a.

On the other hand, when a rightful manager who controls the endoscope 100 collects the reusable portion R including the imaging unit 120, he/she breaks the breaking section 114 or the tube 110a and easily ejects the imaging unit 120 and the small LED lighting 127. The reusable portion R including the ejected imaging unit 120 is cleaned and sterilized so as to be reused.

The imaging element 124 and the small LED lighting 127 of the imaging unit 120 have similar performances to an imaging element and a small LED lighting used in an imaging unit of a general reusable endoscope. Since the imaging unit 120 including such high-performance imaging element 124 and small LED lighting 127 are expensive, after the used endoscope 100 is collected from a user, those members are ejected by the manager of the endoscope 100, and then, cleaned, sterilized, and disinfected to be reused.

The inexpensive single-use portion S including the tube 110a is, for example, discarded and incinerated. The resin included in the single-use portion S may be, for example, dissolved to be reused as a raw material. In other words, with the reusable portion R including the imaging unit 120 that is cleaned, sterilized, and disinfected, and with the single-use portion S including a brand-new tube 110a, a new endoscope 100 is produced and repeatedly provided to a user.

When at least a part of the tube 110a includes a porous resin, it is possible to improve flexibility and pliability of a porous resin portion more than flexibility and pliability of a non-porous portion not including the porous resin. Accordingly, it is possible to improve operability and insertability of the insertion unit 110.

As described above, the porous resin may have a porosity changing in the axial direction or the radial direction of the tube 110a. With an increase in porosity, the porous resin improves in flexibility and pliability but increases in liquid permeability. On the other hand, with a decrease in porosity, the porous resin decreases in flexibility and pliability but improves in liquid barrier property.

Therefore, for example, in the axial direction or in a longitudinal direction of the insertion unit 110, a change in porosity of the porous resin included in the tube 110a changes the flexibility and pliability. In addition, in the radial direction of the insertion unit 110, a change in porosity of the porous resin included in the tube 110a improves the flexibility and pliability of the insertion unit 110 while preventing liquid infiltration.

Specifically, for example, it is possible to decrease the porosity of the porous resin included in the tube 110a from the radially inner side to the outer side of the insertion unit 110, or to decrease the porosity of the porous resin included in the tube 110a from the radially outer side to the inner side of the insertion unit 110.

In addition, as described above, the endoscope 100 according to this embodiment is provided with the rigid member that is inserted through the channels 110b of the tube 110a and the angle wire that is inserted through the rigid member and connected to the bending mechanism of the bending section 112. The operation unit 130 is configured to operate the angle wire. Accordingly, it is possible to operate the angle wire by the operation unit 130 and to bend the bending mechanism by the angle wire. Therefore, the bending section 112 is bent freely by the operation of the operation unit 130.

As described above, the rigid member inserted through the channels 110b of the tube 110a has, for example, flexural rigidity higher than that of the tube 110a, and the rigid member is inserted through the channels 110b in the flexible section 113 closer to the proximal end than the bending section 112. With this rigid member, the channels 110b are protected by the flexible section 113 closer to the proximal end than the bending section 112, which prevents the channels 110b from being damaged by the guide wire. In addition, it is possible to improve the flexural rigidity of the flexible section 113 by the rigid member inserted through the channels 110b of the tube 110a and to improve operability and insertability when the insertion unit 110 is inserted through the body of a patient.

As described above, according to this embodiment, it is possible to provide the endoscope 100 and the endoscope system 1 that enable cost containment without deteriorating operability and insertability.

<First Modification of Endoscope>

Figure 7A:
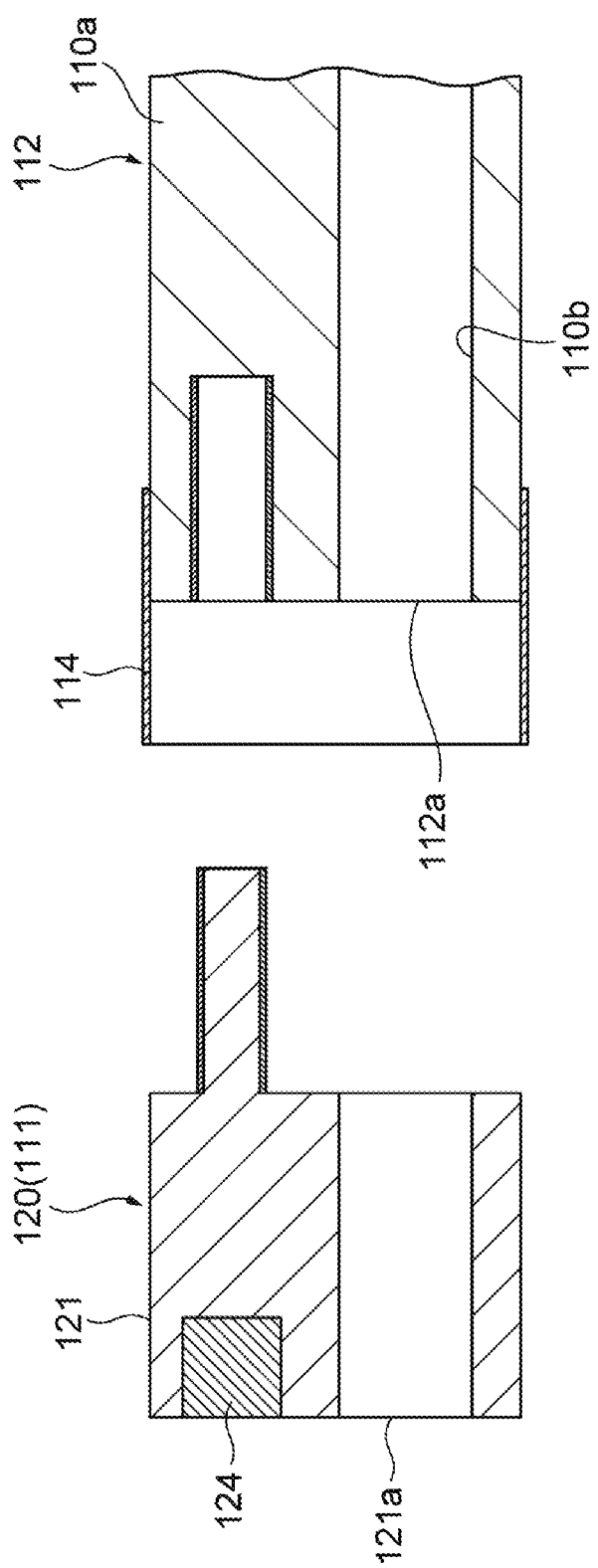
FIG. 7A is an enlarged cross-sectional view illustrating a first modification of the endoscope illustrated in FIGS. 1 and 2.
Figure 7B:
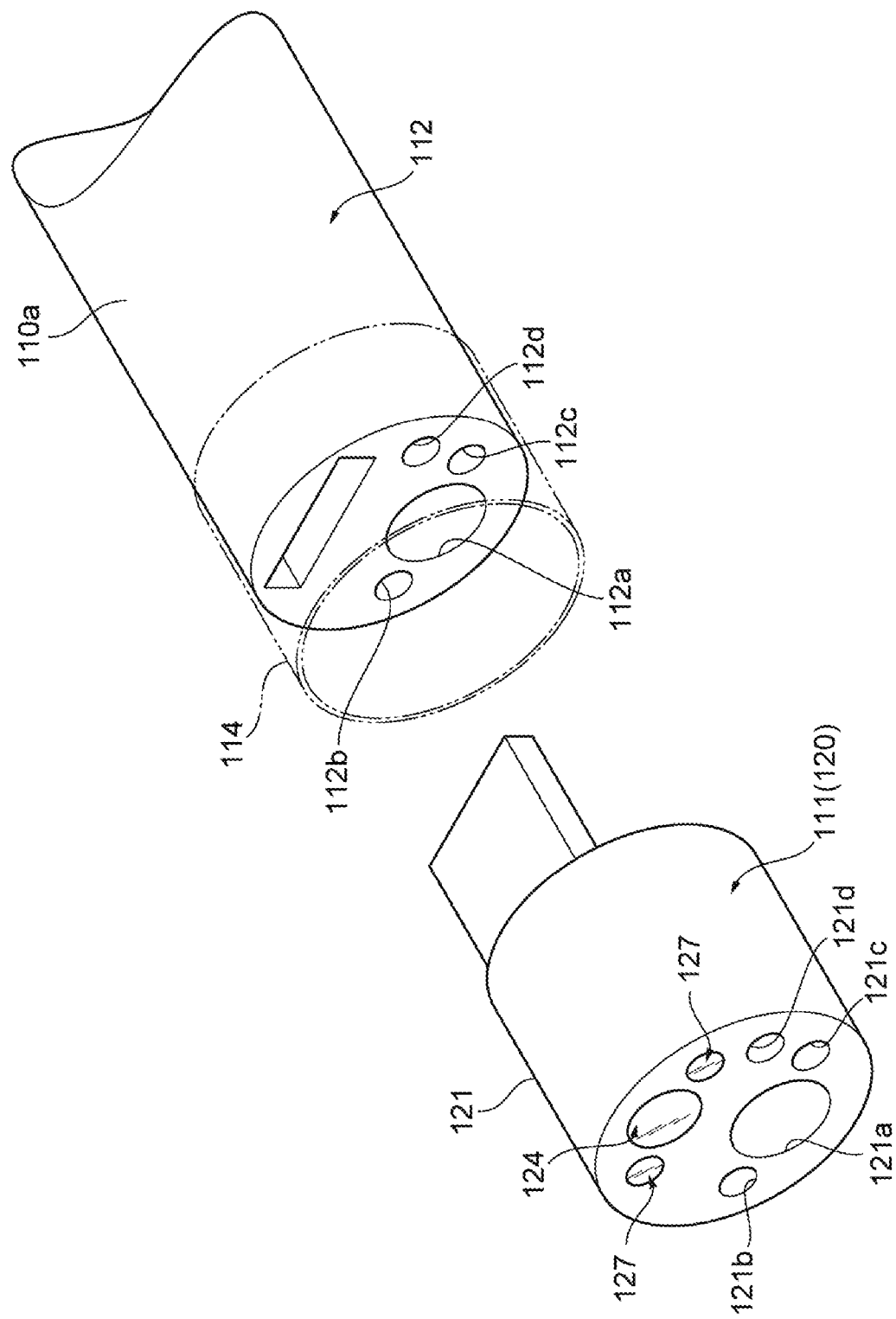
FIG. 7B is an enlarged perspective view illustrating the first modification of the endoscope illustrated in FIGS. 1 and 2.

FIG. 7A is an enlarged cross-sectional view illustrating a first modification of the endoscope 100. FIG. 7B is an enlarged perspective view illustrating the first modification of the endoscope 100. The endoscope 100 according to the first modification is an example where electric power is transmitted to the imaging unit 120 by electric-field coupling.

<Second Modification of Endoscope>

Figure 8B:
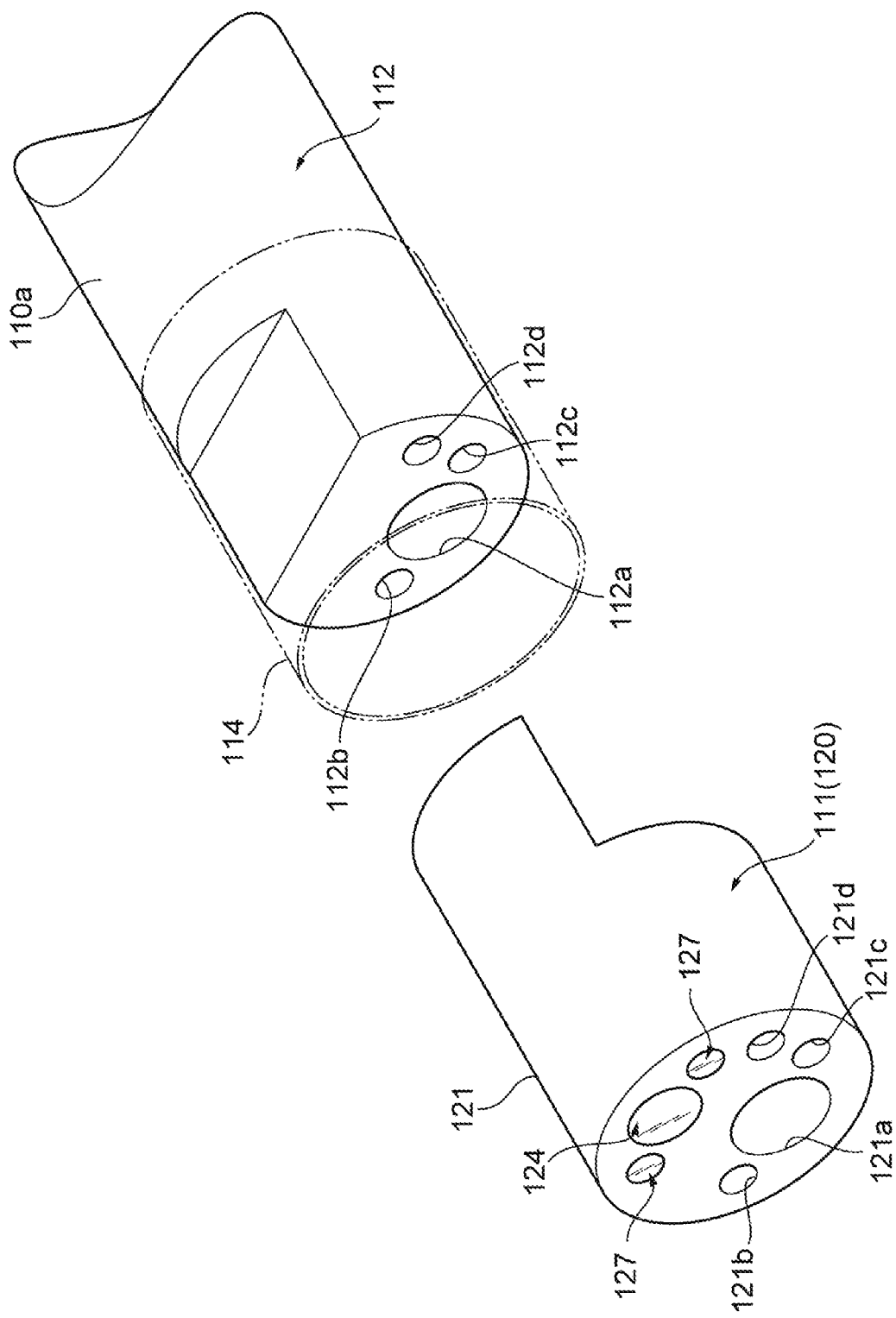
FIG. 8B is an enlarged perspective view illustrating the second modification of the endoscope illustrated in FIGS. 1 and 2.
Figure 9A:
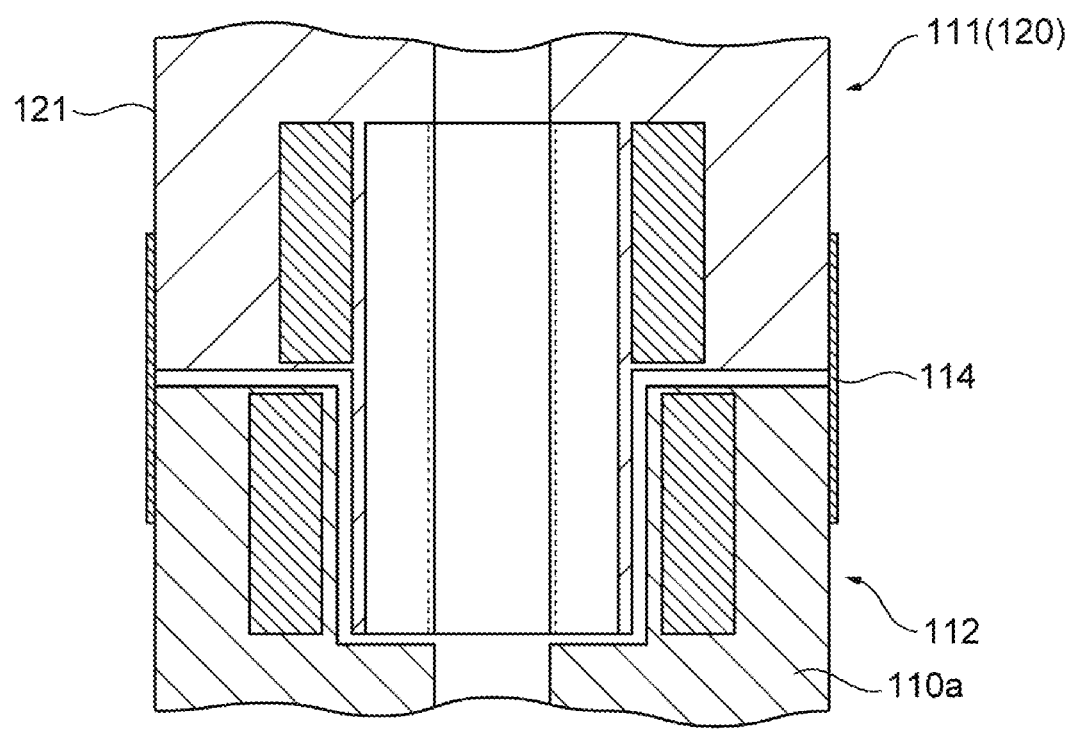
FIG. 9A is an enlarged cross-sectional view illustrating a third modification of the endoscope illustrated in FIGS. 1 and 2.
Figure 9B:
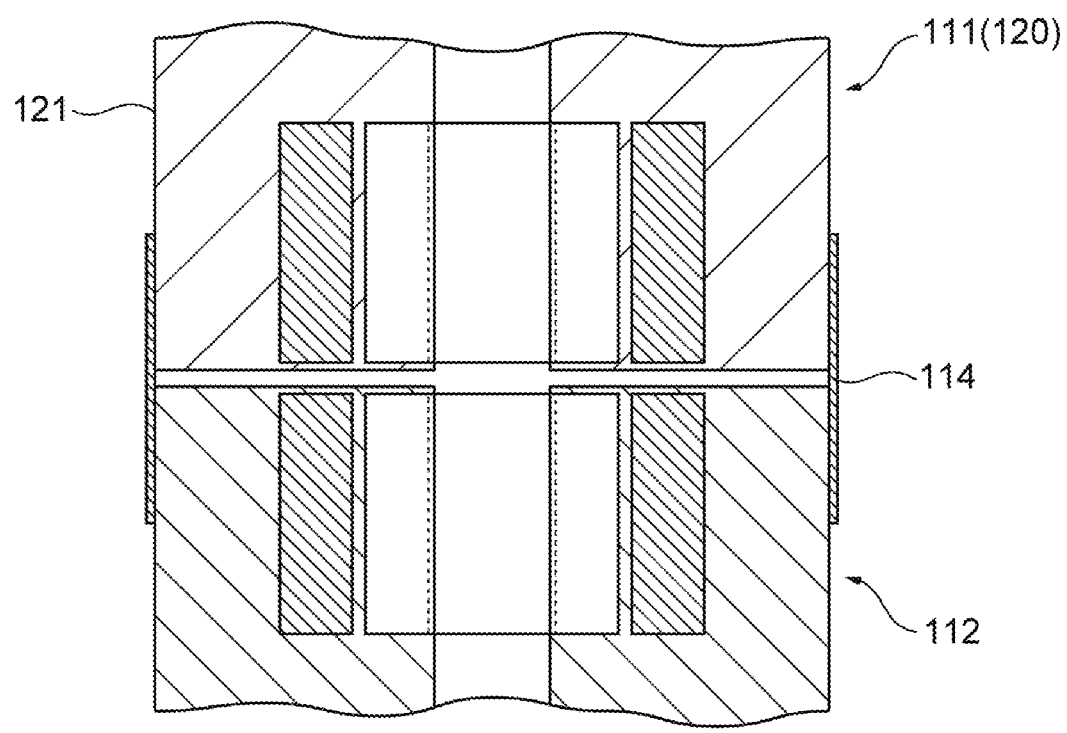
FIG. 9B is an enlarged cross-sectional view illustrating the third modification of the endoscope illustrated in FIGS. 1 and 2.
Figure 9C:
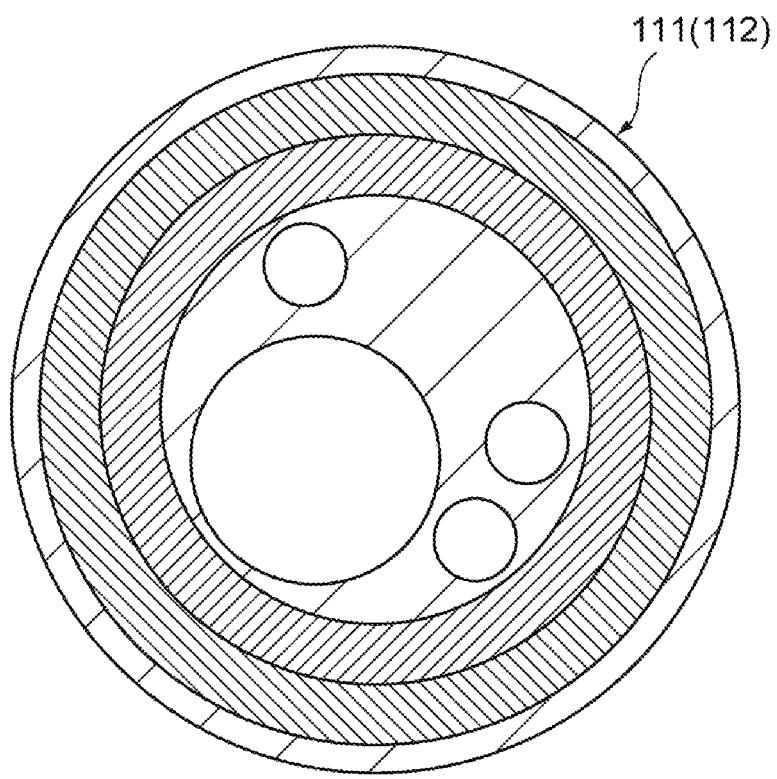
FIG. 9C is an enlarged cross-sectional view illustrating the third modification of the endoscope illustrated in FIGS. 1 and 2.
Figure 9D:
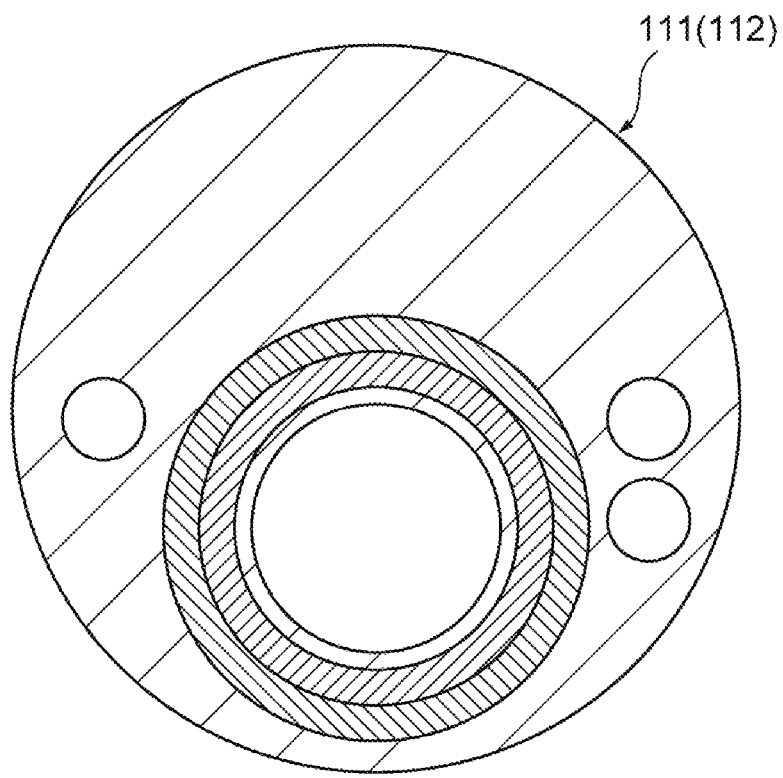
FIG. 9D is an enlarged cross-sectional view illustrating the third modification of the endoscope illustrated in FIGS. 1 and 2.

FIG. 8A is an enlarged cross-sectional view illustrating a second modification of the endoscope 100. FIG. 8B is an enlarged perspective view illustrating the second modification of the endoscope 100. The endoscope 100 of the second modification is an example where electric power is transmitted to the imaging unit 120 by two-dimensional communication (evanescent waves).

<Third Modification of Endoscope>

FIGS. 9A to 9D are cross-sectional views illustrating a third modification of the endoscope 100. The endoscope 100 according to the third modification is an example where electric power is transmitted to the imaging unit 120 by electromagnetic induction. According to the endoscope 100 of this modification, electric power is transmitted from a power transmission coil of the bending section 112 to a power reception coil of the imaging unit 120 by electromagnetic induction.

<Fourth Modification of Endoscope>

Figure 10A:
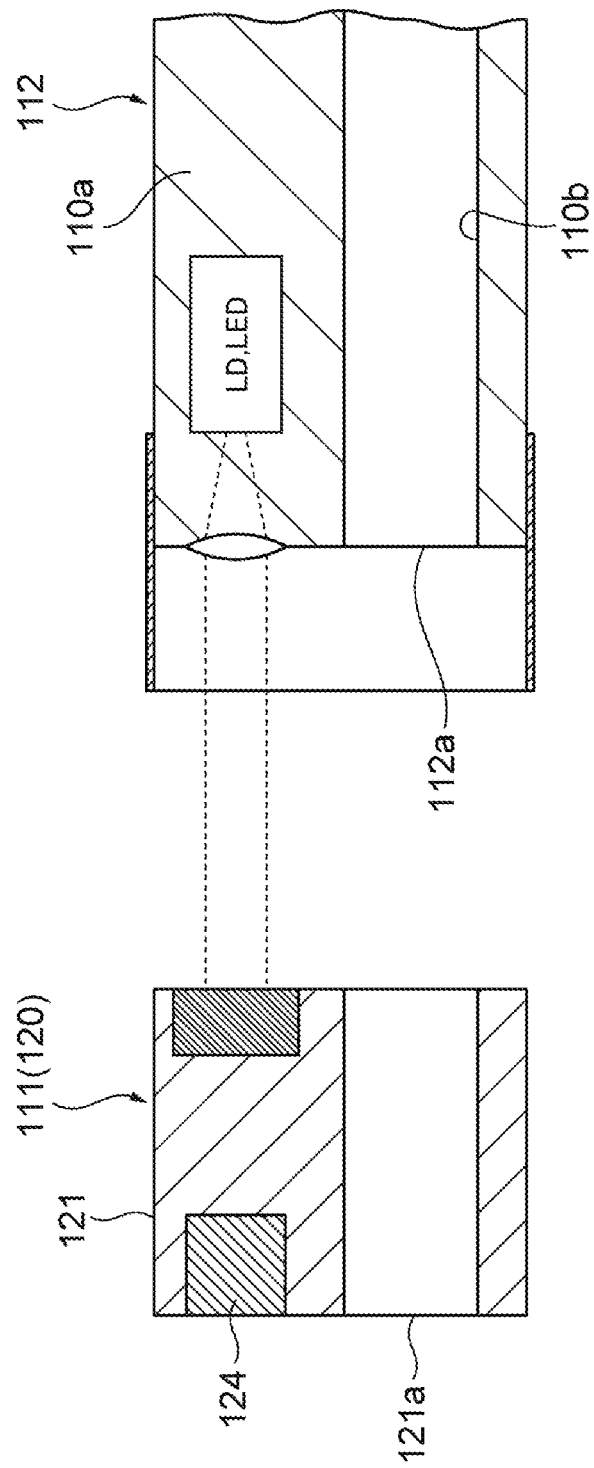
FIG. 10A is an enlarged cross-sectional view illustrating a fourth modification of the endoscope illustrated in FIGS. 1 and 2.
Figure 10B:
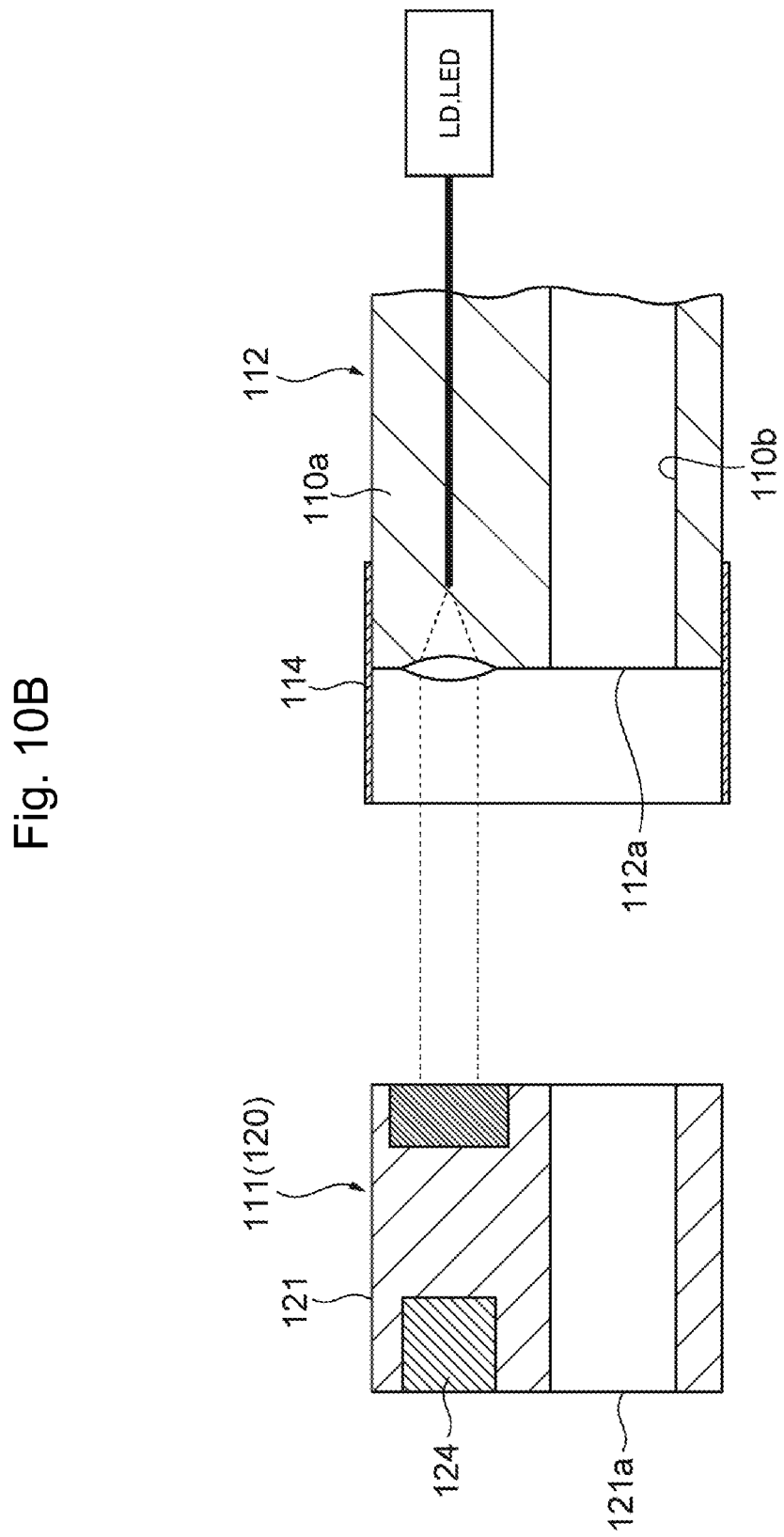
FIG. 10B is an enlarged cross-sectional view illustrating the fourth modification of the endoscope illustrated in FIGS. 1 and 2.

FIGS. 10A and 10B are cross-sectional views illustrating a fourth modification of the endoscope 100. The endoscope 100 according to the fourth modification is an example where electric power or a signal is transmitted by optical transmission.

<Fifth Modification of Endoscope>

FIG. 11 is a cross-sectional view illustrating a fifth modification of the endoscope 100. The endoscope 100 of the fifth modification may transmit electric power or a signal by wireless transmission.

Although preferred embodiments of the present disclosure have been described, the present disclosure is not limited to the embodiments. Some configurations may be added, omitted, substituted, and modified without departing from the gist of the present disclosure. The present disclosure is not limited by the foregoing description except as by the scope of the appended claims.

REFERENCE SIGNS LIST

100 Endoscope
110 Insertion unit
110a Tube
110b Channel
111 Distal tip
112 Bending section
113 Flexible section
114 Breaking section
120 Imaging unit
130 Operation unit
S Single-use portion
R Reusable portion

The invention claimed is:

1. An endoscope comprising:
an insertion unit including an imaging unit; and
an operation unit configured to bend a part of the insertion unit,
wherein at least a part of the insertion unit includes a tube formed of a resin, the tube including a plurality of channels formed of the resin included in the tube,
wherein the resin forms a non-porous resin layer having a porosity of 0%,
wherein the non-porous resin layer is provided on a radially outer surface of the tube and in a part of the tube close to the outer surface,
the endoscope comprising:
a single-use portion including the tube that is replaced for each use; and
a reusable portion including the imaging unit that is collected for each use to be reused
wherein at least a part of the resin is a porous resin, wherein the porous resin has a porosity changing in a radial direction of the tube and the outer surface of the tube have a porosity smaller than that of the center of the tube.

2. The endoscope according to claim 1, wherein the porous resin has a porosity changing in an axial direction of the tube.

3. The endoscope according to claim 2, wherein the insertion unit includes a distal tip including the imaging unit, a bending section that is bent by the operation unit, and a flexible section disposed between the bending section and the operation unit, and
wherein the resin in the bending section has an average porosity larger than an average porosity of the resin in the flexible section.

4. The endoscope according to claim 3, wherein the endoscope comprises a rigid member inserted through one of the plurality of channels and an angle wire inserted through the rigid member and connected to a bending mechanism of the bending section, and
the operation unit is configured to operate the angle wire.

5. The endoscope according to claim 1, wherein the insertion unit includes a distal tip including the imaging unit, a bending section that is bent by the operation unit, and a flexible section disposed between the bending section and the operation unit,
the endoscope comprises a rigid member inserted through one of the plurality of channels and an angle wire inserted through the rigid member and connected to a bending mechanism of the bending section, and
the operation unit is configured to operate the angle wire.

6. The endoscope according to claim 5, wherein the rigid member has flexural rigidity higher than flexural rigidity of the tube, being inserted through the channels in the flexible section.

7. The endoscope according to claim 5, wherein the distal tip includes a plurality of ports including a forceps port, an air supply port, a water supply port, and a secondary water supply port.

8. The endoscope according to claim 1, wherein the insertion unit includes a breaking section that is broken when the imaging unit is removed.

* * * * *